(12) United States Patent
Wietelmann et al.

(10) Patent No.: US 6,261,482 B1
(45) Date of Patent: Jul. 17, 2001

(54) METHOD FOR PRODUCING ORGANO-ALKALI METAL COMPOUNDS

(75) Inventors: Ulrich Wietelmann, Friedrichsdorf; Peter Rittmeyer, Sulzbach; Uwe Lischka, Frankfurt am Main, all of (DE)

(73) Assignee: Metallgesellschaft Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/423,344

(22) PCT Filed: Jun. 2, 1998

(86) PCT No.: PCT/EP98/03267

§ 371 Date: Jan. 3, 2000

§ 102(e) Date: Jan. 3, 2000

(87) PCT Pub. No.: WO98/57974

PCT Pub. Date: Dec. 23, 1998

(30) Foreign Application Priority Data

Jun. 14, 1997 (DE) .............................................. 197 25 192

(51) Int. Cl.$^7$ ................................. C07F 1/02; C07F 1/04; C07F 1/06
(52) U.S. Cl. ........................................................ 260/665 R
(58) Field of Search ........................................... 260/665 R

(56) References Cited

U.S. PATENT DOCUMENTS

| | | | |
|---|---|---|---|
| 2,966,526 | * 12/1960 | Hanley et al. | 260/665 R |
| 2,999,109 | * 9/1961 | Nobis | 260/665 R |
| 3,225,110 | * 12/1965 | Kurtz | 260/665 R |

FOREIGN PATENT DOCUMENTS

| | | |
|---|---|---|
| 1227425 | 7/1971 | (GB). |
| 2083041 | 3/1982 | (GB). |
| 9523803 | 9/1995 | (WO). |

OTHER PUBLICATIONS

Chem. Absts. vol. 121. No. 15—Oct. 10, '94; Liu Preparation of alkali metal derivatives of indene and fluorine.

Chem. Absts. vol. 117. No. 7, Aug. 17, '92—Zhao "An Improved Method for the Preparation of Cyclopentadienyl sodium".

* cited by examiner

*Primary Examiner*—Jean F. Vollano
(74) *Attorney, Agent, or Firm*—Fulbright & Jaworski, LLP

(57) ABSTRACT

The invention relates to a method for producing organo alkali-metal compounds by reacting metal lithium, sodium or potassium with organic compounds containing at least one acidic CH bond in a solvent. The inventive method is characterized in that the reaction is carried out in the presence of a hydrogen acceptor, wherein 0.5 to 5 moles of the hydrogen acceptor are used per mole of acid hydrogen, which hydrogen can be replaced by lithium, sodium or potassium, whereby 1 to 3, moles of lithium, sodium or potassium are used per mole of acid hydrogen and the acid CH bond has a $pK_a$ value of 10 to 30. Cyclopentadiene, indene, fluorene and substitution products thereof, or monosubstituted alkynes or methane substitution products, are preferred CH acid organic compounds. Hydrocarbons used as hydrogen acceptors include these with at least one CC double bond in conjugation with either another CC double bond or with a monocyclic aryl radical.

15 Claims, No Drawings

METHOD FOR PRODUCING ORGANO-ALKALI METAL COMPOUNDS

This application is the national stage of PCT/EP98/03267 filed Jun. 2, 1998 now, WO98/57974.

The invention relates to a process for the preparation of organo-alkali metal compounds by reaction of metallic lithium, sodium or potassium or of alloys of these alkali metals with an organic compound which has at least one acid CH bond in a solvent.

There are diverse possible uses for organo-alkali metal compounds in organic syntheses. Some organo-alkali metal compounds are therefore prepared on an industrial scale and are commercially obtainable in relatively large amounts. Organo-alkali metal compounds are usually prepared by reaction of organic halides with an alkali metal in a solvent in accordance with the equation

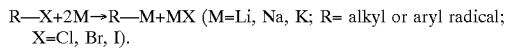

It is furthermore known that acidic hydrogen in organic compounds can be replaced by alkali metals by reaction with strong organometallic bases (e.g. butyllithium), with alkali metal amides (e.g. lithium amide or sodium amide) or with alkali metal hydrides (e.g. sodium hydride).

In the case of sufficiently acidic CH bonds, the metallization can also be carried out directly by means of alkali metals in elemental form. 9-Fluorenyllithium is thus prepared by reaction of fluorene with metallic lithium in tetrahydrofuran (see Houben-Weyl, Methoden der Organischen Chemie [Methods of Organic Chemistry], volume 13/1, Metallorganische Verbindungen [Organometallic compounds], pages 97 to 98, G. Thieme Verlag, Stuttgart, 1970). In the metallization of CH-acid compounds with alkali metals, however, undesirable by-products are as a rule formed if multiple bonds are present in the organic compound to be metallized. These are hydrogenated to a certain extent, which depends on the CH-acid compound, the solvent and the temperature. It has thus been found, for example, that partly hydrogenated fluorenes (e.g. tetrahydrofluorene) are formed as by-products in the lithiumization of fluorene (see Eisch and Kaska, J. Org. Chem. 27, 1962, pages 3745 to 3752). It is furthermore known that the metallization reaction often proceeds only very slowly. For this reason, high excesses of alkali metal are employed as a rule, which is a disadvantage, inter alia, because of the relatively high metal prices. The yields which can be achieved in direct metallization can therefore be described as only moderate for the abovementioned reasons. The yield in the preparation of 9-fluorenyllithium is thus only 71% even if an approx. 6-fold excess of lithium is employed (see Houben-Weyl, above reference).

The invention is therefore based on the object of providing a process for the preparation of organo-alkali metal compounds in which the reaction of the alkali metals lithium, sodium or potassium or alloys thereof with a CH-acid organic compound is carried out such that the formation of undesirable by-products is suppressed, the rate of reaction is increased and the yield of product is increased.

The object underlying the invention is achieved by carrying out that the abovementioned reaction in the presence of a hydrogen acceptor, with 0.5 to 5 mol of the hydrogen acceptor being employed per mol of acid hydrogen which can be replaced by lithium, sodium or potassium, with 1 to 3 mol of lithium, sodium or potassium being employed per mol of acid hydrogen, and with the acid CH bond having a $pk_a$ value of 10 to 30.

Of the alkali metals mentioned, lithium and sodium are preferred for carrying out the process according to the invention, since these two metals are obtainable both in relatively large amounts and relatively inexpensively. Moreover, the compounds metallized with lithium and sodium are relatively stable both to heat and to the solvents employed. Hydrogen acceptors which are used are organic compounds which add on the hydrogen replaced by the alkali metals. The alkali metals present in the process according to the invention do not act as hydrogen acceptors. It has been found that those CH-acid compounds in which the acidity constants $pk_a$ are in the range between 10 and 30 can be metallized by the process according to the invention. The numerical values of the acidity constant which are to be found in the literature vary to a relatively high degree, since they depend on the method of determination and specifically on the solvent chosen and the temperature (see Houben-Weyl, Methoden der Organischen Chemie [Methods of Organic Chemistry], volume VIII/I, 1970, pages 31 to 69). For the classes of compounds of relevance here, acidity constants which have been determined in aqueous solutions are unsuitable per se, since the organo-alkali metal compounds prepared by the process according to the invention are decomposed by water. Rather, only the values of the acidity constants which have been determined in investigations in organic aprotic solvents are relevant for carrying out the process according to the invention, it being acceptable to estimate the $pk_a$ values for a particular solvent if $pk_a$ values for the solvents which have analogous properties are known. The publication by Houben-Weyl cited contains several tables in which the acidity constants $pk_a$ for various solvents are stated, so that—also using primary literature—sufficiently accurate information is available in respect of the acidity constants $pk_a$ of the individual CH-acid compounds.

The process according to the invention has the advantage that the organo-alkali metal compounds can be prepared in a high yield and that the formation of by-products is severely restricted, this being attributed to the synergistic interaction of the CH-acid compounds of particular acidity used and the hydrogen acceptors used. In particular, the undesirable hydrogenation of the multiple bonds present in the molecule of the CH-acid compounds is very severely suppressed in the process according to the invention, and the rate of the metallization reaction is increased in an advantageous manner.

The process according to the invention furthermore has the advantage that it allows the use of elemental alkali metals, which is substantially more inexpensive than the use of the known and conventional metallizing agents, such as butyllithium, lithium hydride or sodium hydride and lithium amide or sodium amide. Furthermore, advantageously no gaseous by-products (e.g. hydrogen) are formed in the process according to the invention, i.e. work safety is increased and emissions are decreased.

According to the invention, it is proposed that the CH-acid organic compound used is cyclopentadiene, indene or fluorene. It is furthermore proposed according to the invention that cyclopentadiene, indene and fluorene are substituted by one or more alkyl radicals and/or monocyclic aryl radicals, each carbon atom of the cyclopentadiene, indene and fluorene having a maximum of only one substituent. It is moreover proposed according to the invention that two molecules of cyclopentadiene and/or indene and/or fluorene or of these compounds substituted by alkyl radicals and/or monocyclic aryl radicals are linked to one another via an alkyl, alkenyl or silyl group. Finally, it is proposed according to the invention that the alkyl substituents and the monocyclic aryl substituents in each case have at least one functional group, the following functional groups being used:

a) di- or trialkylmetal functions; $R_2M=$ or $R_3M—$; M=Si, Ge, Sn; R=alkyl radical
b) fluorine-containing functions; F—, $C_6F_5$, —$CF_3$
c) carboxylic acid derivative functions; —COOR, —CN, —$CONR_2$; R=H, alkyl radical and/or monocyclic aryl radical
d) amine functions; —$NR_2$; R=H, alkyl radical and/or monocyclic aryl radical
e) alkoxy functions; RO—; R=alkyl radical or monocyclic aryl radical
f) nitro function; —$NO_2$.

The CH-acid compounds cyclopentadiene, indene and fluorene are used for carrying out the process according to In these compounds, the hydrogen atoms of the $CH_2$ group have an acid character and are therefore accessible for metallization. The substitution products of these compounds, which can likewise be used for carrying out the process according to the invention, contain one or more alkyl and/or monocyclic aryl substituents. These radicals replace the hydrogen atoms contained in the rings of the compounds and/or the second hydrogen atom of the $CH_2$ group.

For example, the second hydrogen atom of the $CH_2$ group in 9-phenylfluorene is replaced by the phenyl radical. Each carbon atom of cyclopentadiene, indene and fluorene has a maximum of only one of the abovementioned substituents. Those CH-acid compounds which consist of two molecules of cyclopentadiene and/or indene and/or fluorene are also accessible to the metallization according to the invention, it being possible for both molecules to be substituted by alkyl radicals and/or monocyclic aryl radicals and the two molecules being linked to one another via an alkyl, alkenyl or silyl group. According to the invention, both symmetric and asymmetric CH-acid compounds can thus be used, i.e. these compounds contain, in addition to the bridge group, either two identical or two different molecules, the molecules being cyclopentadiene, indene and/or fluorene. The alkyl substituents or the monocyclic aryl substituents of cyclopentadiene, indene and fluorene can in turn have different functional groups, some of these functional groups being capable of linking two acid CH-compounds, such as e.g. the functional group $R_2M=$.

It has been found that the abovementioned compounds are metallized by the process according to the invention virtually exclusively (>90%) on the acid $CH_2$ or CHR group of the ring skeleton, and otherwise remain largely unchanged. In contrast, if a hydrogen acceptor is omitted hydrogenation products which are also present to some extent in metallized form are formed. The undesirable hydrogenation products are e.g. cyclopentene or di- and tetrahydrofluorene or the corresponding substituted hydrogenation products.

Alternatively, it is proposed according to the invention that the CH-acid compound used is a monosubstituted alkyne R—C≡C—H, wherein R is an alkyl substituent or a monocyclic aryl substituent. In this case, it is proposed according to the invention that the alkyl substituents and monocyclic aryl substituents of the alkyne in each case contain at least one functional group, the following functional groups being used:

a) fluorine-containing functions; F—, $C_6F_5$, —$CF_3$
b) carboxylic acid derivative functions; —COOR, —CN, —$CONR_2$; R=H, alkyl radical and/or monocyclic aryl radical
c) amine functions; —$NR_2$; R=H, alkyl radical and/or monocyclic aryl radical
d) alkoxy functions; RO—; R=alkyl radical or monocyclic aryl radical
e) nitro function; —$NO_2$.

It has been found that the metallized products R—C≡C—M (M=alkali metal) are obtained in an almost pure form in the process according to the invention, while in the reaction of alkynes with alkali metals in the absence of a hydrogen acceptor the hydrogenation products, that is to say the corresponding olefins $RHC=CH_2$, to some extent also in metallized form, are formed.

Finally, as a further alternative it is proposed according to the invention that the CH-acid organic compound used is a compound having the structure

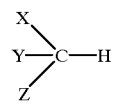

wherein at least one group X, Y, Z is a carboxylic acid, ester, carboxylic acid amide, nitrile, isonitrile, carbonyl, nitro, trifluoromethyl or pentafluorophenyl group, and wherein the other groups X, Y, Z independently of one another are hydrogen, alkyl radicals and/or monocyclic aryl radicals. For this alternative it is proposed according to the invention that the groups X, Y, Z consisting of alkyl radicals or monocyclic aryl radicals in turn contain at least one functional group, the following functional groups being used:

a) fluorine-containing functions; F—, $C_6F_5$, —$CF_3$
b) carboxylic acid derivative functions; —COOR, —CN, —$CONR_2$; R=H, alkyl radical and/or monocyclic aryl radical
c) amine functions; —$NR_2$; R=H, alkyl radical and/or monocyclic aryl radical
d) alkoxy functions; RO—; R=alkyl radical or monocyclic aryl radical
e) nitro function; —$NO_2$.

The CH-acid compounds of the type XYZCH can be regarded as derivatives of methane, wherein at least one group X, Y, Z contains a heteroatom, which can also be linked to the molecule via a multiple bond, and wherein the other groups X, Y, Z are hydrogen, alkyl radicals and/or monocyclic aryl radicals. The alkyl radicals and monocyclic aryl radicals can in turn contain various functional groups. The derivatives of methane which are suitable for carrying out the process according to the invention are as a rule metallized with yields of >90% without the multiple bonds contained in the molecule being hydrogenated to a noticeable extent. A typical representative of the compound type XYZCH is acetonitrile $CH_2CN$.

All the carboxylic acid, ester, carboxylic acid amide, nitrile, isonitrile, carbonyl, nitro, trifluoromethyl, pentafluorophenyl, fluorine and alkoxy groups contained in the CH-acid compounds have the common feature that they increase the acidity of the CH-acid compounds to a greater or lesser degree, since they have an electrophilic, electron-withdrawing action. All the monocyclic aryl radicals consist of a phenyl group or a phenyl group substituted by one or more alkyl radicals.

According to the invention, it is furthermore proposed that the hydrogen acceptor used is a hydrocarbon which has at least one CC double bond which is in conjugation either with another CC double bond or with a monocyclic aryl radical. Alternatively, according to the invention it is proposed that ortho-condensed, polycyclic aromatics are used as the hydrogen acceptor. According to the invention, it has proved particularly advantageous if 1,3-butadiene, isoprene, conjugated polyenes, 1,3-cyclohexadiene, styrene, naphthalene, anthracene, phenanthrene or mixtures of these compounds are used as the hydrogen acceptor.

Particularly preferred hydrogen acceptors are isoprene, styrene and naphthalene, since these compounds are both inexpensive and easy to handle. The hydrogenation products of these hydrogen acceptors can be separated off from the reaction mixture or remain in the reaction mixture as the solvent. If the particularly preferred hydrogen acceptors are used, the reaction can be carried out close to the theoretical stoichiometry (0.5 mol of hydrogen acceptor per mol of CH-acid compound) without there being adverse effects on the yield. However, it is also possible to use the hydrogen acceptor in a higher excess, it either being separated off or remaining in the solvent when the metallization reaction has ended. If the metallization reaction is carried out in the presence of styrene, ethylbenzene, which is particularly suitable as the solvent, is formed by addition of the hydrogen. The hydrogenation of the hydrogen acceptor proceeds rapidly and exothermically, as a result of which the rate of the metallization reaction is also increased. The hydrogen acceptors to be used according to the invention add on the hydrogen at a higher rate than the CC multiple bonds contained in the CH-acid compounds and/or the multiple bonds originating from the heteroatoms. This fact is surprising to the expert, because the CC multiple bonds contained in the CH-acid compounds and the multiple bonds originating from the heteroatoms have heats of hydrogenation which are similar to and in some cases even higher than those of the hydrogen acceptors to be used according to the invention. The ortho-condensed polycyclic aromatics used as hydrogen acceptors consist of at least two 6-membered rings, the rings being linked along the edges. Thus in phenanthrene, the third 6-membered ring is linked along the edge with the other two 6-membered rings in each case via a common CC bond.

According to the invention, it has proved particularly advantageous if the metallic lithium, sodium and potassium and the alloys of these metals are employed in the form of granules or powders with an average particle diameter $d_{50}$ of <0.1 mm. The alkali metals are particularly reactive in this form, since the metallization reaction proceeds in the solid/liquid interface of the alkali metal and the large surface area of the finely divided granules and powders promotes the metallization reaction. In addition, as a rule no insoluble by-products which could block the surface of the alkali metals are formed in the metallization reaction according to the invention. This is an advantage over the known synthesis of organo-alkali metal compounds from organic halides, in which the alkali metal halides formed at least partly block the metal surface.

According to the invention, it is furthermore proposed that ethers or monocyclic aromatic hydrocarbons are used as the solvent, at least two mol of ether advantageously being present per mole of the CH-acid organic compound. According to the invention it is particularly advantageous if the ethereal solutions are diluted with saturated hydrocarbons and/or with monocyclic aromatic hydrocarbons. It is particularly advantageous if diethyl ether, 1,2-dimethoxyethane, methyl tert-butyl ether, diisopropyl ether or tetrahydrofuran are used as ethers, pentane, hexane, cyclohexane and/or heptane are used as saturated hydrocarbons, and toluene, xylene and/or ethylbenzene are used as monocyclic aromatic hydrocarbons. As a rule, a solvent which comprises 10 to 80 wt. % of an ether and 90 to 20 wt. % of at least one saturated hydrocarbon having 5 to 10 C atoms and/or of at least one monocyclic aromatic hydrocarbon can be used.

Finally, it is proposed according to the invention that the reaction temperature is in the range from −20 to 150° C., preferably in the range from 10 to 70° C. The high reaction temperatures are used only if the organo-alkali metal compounds are very stable to heat and if higher-boiling components are to be separated off from the reaction mixture. At the abovementioned reaction temperatures, the process according to the invention can also be controlled reliably on an industrial scale.

The organo-alkali metal compounds prepared by the process according to the invention either can be marketed in the form of their solution, or can be used directly after preparation for carrying out an organic synthesis. The product solutions can be used, for example, in metallocene chemistry or for the preparation of intermediate products for pharmaceuticals. Fluorenyllithium can be used, for example, for synthesis of 9-fluorenylmethanol by reaction with formaldehyde.

The following table contains values of the acidity constants $pk_a$ for some CH-acid organic compounds which can be metallized by the process according to the invention. The solvents or the methods in or by which the $pk_a$ values have been determined are also stated in the table.

TABLE

| CH-acid compound | pk$_a$ value | Solvent/Method |
|---|---|---|
| CH$_2$(CN)$_2$ | 11.0 | in dimethylsulfoxide |
| Diethyl malonate | 15.8 | acc. to J. Chim. Phys. 52, p. 784, 1955 |
| Nitromethane | 17.2 | in dimethylsulfoxide |
| Cyclopentadiene | 17.9 | in dimethylsulfoxide |
| Acetophenone | 19.0 | acc. to McEwen |
| Indene | 21.0 | acc. to McEwen |
| 9-Phenylfluorene | 18.5 | in cyclohexylamine |
| Fluorene | 22.9 | in tetrahydrofuran |
| Phenylacetylene | 23.2 | in cyclohexylamine |

The subject matter of the invention is explained in more detail below with the aid of several embodiment and comparison examples.

EXAMPLE 1

2.95 g (426 mmol) lithium granules in 305 g tetrahydrofuran were initially introduced into a double-jacketed reactor which could be cooled. A mixture of 200 g tetrahydrofuran, 22.1 g (212 mmol) styrene and 66.47 g (400 mmol) fluorene was metered in over a period of 75 minutes. During this operation, the reaction temperature was kept at 40° C. by cooling; the reaction proceeded exothermically. The mixture was then stirred at 30° C. for one hour, and thereafter the dark red solution was filtered. The residue on the filter was washed with a little tetrahydrofuran, and the wash liquid was combined with the filtrate. The yield of fluorenyllithium was 94.5%, based on the fluorene employed.

Comparison Example A

This comparison example was carried out in accordance with Example 1, but no styrene was added. Hydrogen was formed during the reaction; however, only 15% of the amount of hydrogen to be expected theoretically was obtained. The yield was 87.5%, based on the fluorene employed. After the hydrolysis of the product solution with water, four by-products were found by gas chromatography and mass spectroscopy methods, these being partly hydrogenated fluorene in which one or two double bonds were hydrogenated. The by-products were present in an amount of 20%, based on the fluorene employed. The contradiction between the yield of 87.5% determined and the content of by-products of 20% is to be explained by the fact that the by-products are also lithiumized to a certain amount and therefore are recorded in the determination of the yield. In fact, the yield of fluorenyllithium was thus not 87.5%, but only approx. 80%. In contrast, the product prepared according to example 1 in the presence of styrene comprised only very small amounts of the by-products which are formed by partial hydrogenation of the fluorene.

EXAMPLE 2

2.59 g (373 mmol) lithium granules in 72 g tetrahydrofuran and 40 g toluene were initially introduced into a double-jacketed reactor which could be cooled. A mixture of 54.9 g (330 mmol) fluorene, 200 g toluene and 18 g (173 mmol) styrene was metered in over a period of 75 minutes. The reaction temperature was kept at 30 to 35° C. by cooling; the reaction proceeded exothermically. The mixture was then stirred for one hour, and thereafter the dark red solution was filtered. The residue on the filter was washed with a little tetrahydrofuran, and the wash liquid was combined with the filtrate. The yield of fluorenyllithium was 85%, based on the fluorene employed.

Comparison Example B

This comparison example was carried out in accordance with Example 2, but without styrene. No evolution of hydrogen was observed during the reaction, and the total yield of organolithium compounds was 67.5%. Of this total yield, only some is due to fluorenyllithium, since the course of the reaction in this comparison examples corresponds to the course of the reaction of comparison Example A.

EXAMPLE 3

2.2 g (317 mmol) lithium powder in 175 g tetrahydrofuran were initially introduced into a double-jacketed reactor which could be cooled. 19.9 g (301 mmol) monomeric cyclopentadiene in 20 g tetrahydrofuran and 15.6 g (150 mmol) styrene in 16 g tetrahydrofuran were metered in simultaneously from two dropping funnels over a period of 60 minutes. The reaction proceeded exothermically. The reaction temperature was kept at 35° C. by cooling. The mixture was then stirred at 35° C. for one hour, and thereafter the bright red solution was filtered. The yield of cyclopentadienyllithium was 91.8%, based on the cyclopentadiene employed.

Comparison Example C

This comparison example was carried out analogously to Example 3, but no styrene was present. In this reaction, hydrogen was formed in an amount of 52%, based on the yield of hydrogen to be expected theoretically. The total yield of the organolithium compounds prepared was 82.6%, based on the cyclopentadiene employed. However, the hydrogenation product cyclopentene, which is likewise accessible to a certain portion of the lithiumization, was identified in the product by gas chromatography and mass spectroscopy methods, so that the yield of cyclopentadienyllithium is actually lower than 82.6%.

EXAMPLE 4

4.95 g (215 mmol) sodium in the form of pieces with an edge length of 5 to 15 mm were initially introduced into 150 g tetrahydrofuran. A mixture of 33.4 g (201 mmol) fluorene, 10.44 g (100.2 mmol) styrene and 100 g tetrahydrofuran was metered in over a period of 45 minutes. The reaction temperature was kept at 40° C. by cooling. The reaction proceeded exothermically. After stirring at room temperature for 7 hours, unreacted sodium was filtered off from the red-coloured solution. The yield of fluroenylsodium was 65.7%.

Comparison Example D

The procedure was analogous to Example 4, but without the addition of styrene. The metallization reaction proceeded very slowly. The yield of fluorenylsodium was only 8%, and it is to be assumed that the reaction solution comprises hydrogenation products of fluorene, since no evolution of hydrogen was observed during the reaction.

EXAMPLE 5

1.054 g (152 mmol) lithium powder were suspended in 85 g tetrahydrofuran. A mixture of 12 g tetrahydrofuran, 6.48 g (62.2 mmol) styrene and 10.16 g (123 mmol) tert-butylacetylene was added to this suspension over a period of 50 minutes. The reaction temperature of the exothermic reaction was kept at 30° C. by cooling. During the reaction, no evolution of gas was observed. After stirring at room temperature for one hour, the slightly yellow-coloured solution was filtered. The yield of lithium tert-butylacetylide was 95.1%, based on the butylacetylene employed. After hydrolysis of the reaction product, it was found by analysis by gas chromatography that tert-butylethylene had been formed by a side reaction, and in particular in an amount of approx. 5%, based on the main product lithium tert-butylacetylide.

Comparison Example E

The procedure was according to Example 5, but without styrene. Hydrogen was formed during the reaction, but only 10% of the amount of hydrogen to be expected theoretically was obtained. The yield was 72.1%. After the hydrolysis of the end product, it was found by an analysis by gas chromatography that tert-butylethylene had been formed in a considerable amount by a hydrogenation side reaction, and in particular the ratio between the main product lithium tert-butylacetylide and the by-product tert-butylethylene was 100:39.

EXAMPLE 6

2.44 g (352 mmol) lithium powder were suspended in 220 g tetrahydrofuran. A mixture of 12.45 g (303 mmol) acetonitrile and 15.62 g (150 mmol) styrene was then added over a period of 30 minutes. The reaction temperature was kept at 25° C. by cooling. The mixture was then stirred at room temperature for a further 90 minutes. Thereafter the unreacted lithium was filtered off. Evolution of hydrogen was observed during the metallization reaction, but only 40% of the amount of hydrogen to be expected theoretically was isolated. The yield of $LiCH_2CN$ was 95%, based on the acetonitrile employed. No hydrogenation products of acetonitrile were to be found in an analysis by gas chromatography; only acetonitrile, ethylbenzene and styrene were identified.

The embodiment and comparison examples show that CH-acid organic compounds can be converted into the corresponding organo-alkali metal compounds with a high yield with the process according to the invention, the formation of by-products in particular, being suppressed considerably. The reaction products resulting from the hydrogen acceptor styrene do not impede the possible uses of the process products, while the by-products formed from the CH-acid compounds all display adverse effects during the further processing of the process product, since the metallized by-products react during further processing of the process product to give undesirable end products. The avoidance of by-products of the metallization is thus to be evaluated as a considerable advantage of the invention.

What is claimed is:

1. A process for the preparation of organo-alkali metal compounds comprising reacting an alkali metal selected from the group consisting of lithium, sodium, potassium and alloys thereof with an organic compound having at least one acidic CH bond and having a $pK_a$ value of from 10 to 30 in a solvent in the presence of a hydrogen acceptor, said hydrogen acceptor being a hydrocarbon which has at least one carbon-carbon double bond which is in conjugation either with another carbon-carbon double bond or with a monocyclic aryl radical, wherein the mole ratio of hydrogen acceptor to the acidic hydrogen in the CH bond ranges from 0.5:1 to 5:1 and the mole ratio of said alkali metal or alloy thereof to the acidic hydrogen is from 1:1 to 3:1.

2. The process according to claim 1, wherein the organic compound is selected from the group consisting of cyclopentadiene, indene and fluorene.

3. The process according to claim 2, wherein said organic compound is substituted by one or more alkyl radicals or monocyclic aryl radicals, each carbon atom of said organic compound having a maximum of only one substituent.

4. The process according to claim 2, wherein two molecules of said organic compound are linked by an alkyl, alkenyl or silyl group.

5. The process according to claim 3, wherein two molecules of said CH-acid organic compound are linked by an alkyl, alkenyl or silyl group.

6. The process according to claim 1, wherein said CH-acid compound is a monosubstituted alkyne R—C≡C—H, wherein R is an alkyl substituent or a monocyclic aryl substituent.

7. The process according to claim 1, wherein said hydrogen acceptor is an ortho-condensed, polycyclic aromatic.

8. The process according to claim 1, wherein said hydrogen acceptor is at least one member selected from the group consisting of 1,3-butadiene, isoprene, conjugated polyenes, 1,3-cyclohexadiene, styrene, naphthalene, anthracene and phenanthrene.

9. The process according to claim 1, wherein said alkali metals and the alloys of these metals are in the form of granules or powders with an average particle diameter of less than 0.1 mm.

10. The process according to claim 1, wherein said solvent is selected from the group consisting of ethers and monocyclic aromatic hydrocarbon.

11. The process according to claim 10, wherein at least two moles of ether are present per mole of organic compound.

12. The process according to claim 10, wherein ethereal solutions are diluted with a member selected from the group consisting of saturated hydrocarbons and monocyclic aromatic hydrocarbons.

13. The process according to claim 10, wherein said solvent is selected from the group consisting of diethyl ether, 1,2-dimethoxyethane, methyl tert-butyl ether, diisopropyl ether, tetrahydrofuran pentane, hexane, cyclohexane, heptane, toluene, xylene and ethylbenzene.

14. The process according to claim 11, wherein said reaction is carried out at temperature range from −20 to 150° C.

15. The process according to claim 14, wherein the reaction temperature ranges from 10 to 70° C.

* * * * *